United States Patent
Ndondo-Lay (12) 
(10) Patent No.: US 6,273,908 B1
(45) Date of Patent: Aug. 14, 2001

(54) STENTS

(76) Inventor: Robert Ndondo-Lay, 8830 Pipestone Way, San Diego, CA (US) 92129

( * ) Notice: Subject to any disclaimer, the term of this patent is extended or adjusted under 35 U.S.C. 154(b) by 0 days.

(21) Appl. No.: 08/957,241

(22) Filed: Oct. 24, 1997

(51) Int. Cl.[7] .................................................. A61P 2/06
(52) U.S. Cl. ............................................ 623/1; 606/194
(58) Field of Search ........................ 623/1, 12; 606/108, 606/192, 194–5

(56) References Cited

U.S. PATENT DOCUMENTS

| | | | |
|---|---|---|---|
| 3,868,956 | 3/1975 | Alfidi et al. | 128/345 |
| 4,503,569 | 3/1985 | Dotter | 3/1.4 |
| 4,512,338 | 4/1985 | Balko et al. | 128/1 R |
| 4,553,545 | 11/1985 | Maass et al. | 128/341 |
| 4,655,771 | 4/1987 | Wallsten | 623/1 |
| 4,665,918 | 5/1987 | Garza et al. | 128/343 |
| 4,733,665 | 3/1988 | Palmaz | 128/343 |
| 4,795,458 | 1/1989 | Regan | 623/1 |
| 4,800,882 | 1/1989 | Gianturco | 128/343 |
| 4,830,003 | 5/1989 | Wolff et al. | 128/343 |
| 4,856,516 | 8/1989 | Hillstead | 128/343 |
| 4,878,906 | 11/1989 | Lindemann et al. | 623/1 |
| 4,886,062 | 12/1989 | Wiktor | 128/343 |
| 4,907,336 | 3/1990 | Gianturco | 29/515 |
| 5,201,757 | 4/1993 | Heyn et al. | 606/198 |
| 5,234,456 | 8/1993 | Silvestrini | 606/194 |
| 5,234,457 | 8/1993 | Andersen | 606/198 |
| 5,292,331 | 3/1994 | Boneau | 606/198 |
| 5,314,444 | 5/1994 | Gianturco | 606/195 |
| 5,342,348 | 8/1994 | Kaplan | 606/891.1 |
| 5,344,426 | 9/1994 | Lau et al. | 606/198 |
| 5,354,309 | * 10/1994 | Schnepp-Pesch et al. | 623/1 |
| 5,368,566 | 11/1994 | Crocker | 604/101 |
| 5,372,600 | 12/1994 | Beyar et al. | 606/198 |
| 5,382,261 | 1/1995 | Palmaz | 606/158 |
| 5,383,928 | 1/1995 | Scott et al. | 623/1 |
| 5,387,235 | 2/1995 | Chuter | 623/1 |

(List continued on next page.)

OTHER PUBLICATIONS

Bailey et al., "Polymer Coating of Palmaz –Schtz Stent Attenuates vascular Spam After Stent Placement" *Circulation* 82:III–541 (1990).

Cavendar et al., "The Ettects of Heparin Bonded Tantalum Stents On Thrombosis and Neointimal Proliferation" *Circulation* 82:III–541 (1990).

de Jaegere et al., "Wiktor Stent Implantation in Patients with Restenosis Following Balloon Angioplasty of a Native Coronary Artery" *Amer. J. Cardiol.* 69:598–602 (1992).

Agrawal et al., "Nonsurgical Closure of Femoral Pseudoaneurysms Compolicating Cardiac Catheterization and Percutaneous Transluminal Coronary Angioplasty" *J. Am. Coll. Cardiol.* 20:610–615 (1992).

van der Giessen et al., "Coronary Stenting with a Radiopaque, Anthrombogenic, Ballon–Expandable Stent" *Circulation* 80:II–173 (1989).

van der Giessen, "Self–expandable Mesh Stents: an Experimental Study comparing Polymer Coated and Uncoated Wallstent in the Coronary Circulation of Pigs" *Circulation* 82:III–542 (1990).

*Primary Examiner*—Bruce E. Snow
(74) *Attorney, Agent, or Firm*—Gray Cary Ware & Freidenrich; Stephen E. Reiter; Ramsey R. Stewart (57) ABSTRACT

A stent having cavities has been developed that can be quickly and easily used in a wide variety of situations, that keeps vessels open with a minimum degree of recoil and shortening lengthwise, that is flexible and can be delivered to the most distal lesion, and that can continuously deliver anticoagulant or other biologically active agents for an extended period directly at the site of stent placement. The stent of the present invention includes at least one flexible, serpentine backbone, and a plurality of opposing, outwardly-projecting appendages on said backbone, wherein said stent has a substantially circular cross-section.

2 Claims, 6 Drawing Sheets

U.S. PATENT DOCUMENTS

| | | | |
|---|---|---|---|
| 5,419,760 | 5/1995 | Narciso, Jr. | 604/8 |
| 5,423,885 | 6/1995 | Williams | 623/1 |
| 5,443,458 | 8/1995 | Eury | 604/891.1 |
| 5,449,373 | 9/1995 | Pinchasik et al. | 606/198 |
| 5,464,450 | 11/1995 | Buscemi et al. | 623/6 |
| 5,464,650 | 11/1995 | Berg et al. | 427/2.3 |
| 5,500,013 | 3/1996 | Busceni et al. | 623/1 |
| 5,540,712 | 7/1996 | Kleshinski et al. | 606/198 |
| 5,545,208 * | 8/1996 | Wolff et al. | 623/1 |
| 5,549,635 | 8/1996 | Solar | 606/198 |
| 5,549,662 | 8/1996 | Fordenbacher | 623/1 |
| 5,556,413 | 9/1996 | Lam | 606/198 |
| 5,591,197 | 1/1997 | Orth et al. | 606/198 |
| 5,593,434 | 1/1997 | Williams | 623/1 |
| 5,599,576 | 2/1997 | Opolski | 427/2.3 |
| 5,603,721 | 2/1997 | Lau et al. | 606/195 |
| 5,605,530 | 2/1997 | Fischell et al. | 600/3 |
| 5,607,467 | 3/1997 | Froix | 623/1 |
| 5,618,299 | 4/1997 | Khosravi et al. | 606/198 |
| 5,632,771 * | 5/1997 | Boatman et al. | 623/1 |
| 5,637,113 | 6/1997 | Tartaglia et al. | 623/1 |
| 5,649,977 | 7/1997 | Campbell | 623/1 |
| 5,651,174 | 7/1997 | Schwartz et al. | 29/527.2 |
| 5,843,120 * | 12/1998 | Israel et al. | 623/1 |

* cited by examiner

STENTS

FIELD OF THE INVENTION

The present invention relates to stents having cavities capable of incorporating biologically active agents therein. More particularly, the present invention relates to stents that are highly flexible, easily used in a wide variety of situations, and that can continuously deliver diagnostic and/or therapeutic agents for an extended period directly at the site of stent placement. In another aspect, the present invention relates to methods of making stents having such properties. Stents according to the present invention are especially useful for vascular treatment.

BACKGROUND OF THE INVENTION

Cardiovascular disease, including atherosclerosis, is the leading cause of death in the United States. The medical community has developed a number of methods for treatment of coronary heart disease, some of which are specifically designed to treat complications resulting from atherosclerosis and other forms of coronary arterial narrowing.

In another form, arterial wall degeneration with the formation of aneurysms causes arterial wall thinning. Management of the dilated arteries in the peripheral circulation has come under the domain of vascular surgeons.

Investigators in the field of vascular surgery had at one time handled both narrowed and dilated arteries by techniques for suture anastomosis (sewing together) of two arterial segments using needle and thread. Today, there is a significantly less invasive clinical approach known as endovascular grafting.

However, the most compelling development in the past decade is percutaneous transluminal coronary angioplasty (PTCA, or simply "angioplasty"). The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions and is related to the nature of the plaque. Soft, fatty plaque deposits are flattened by the balloon and hardened deposits are cracked and split to enlarge the lumen. The wall of the artery itself is stretched when the balloon is inflated.

PTCA is performed as follows: A thin walled, hollow guiding catheter is typically introduced into the body via a relatively large vessel, such as the femoral artery in the groin area or the brachial artery in the arm. Access to the femoral artery is achieved by introducing a large bore needle directly into the femoral artery, a procedure known as the Seldinger technique. Once access to the femoral artery is achieved, a short hollow sheath is introduced to maintain a passageway during PTCA. The flexible guiding catheter, which is typically polymer coated, and lined with Teflon™, is inserted through the sheath into the femoral artery. The guiding catheter is advanced through the femoral artery into the iliac artery and into the ascending aorta. Further advancement of the flexible catheter involves the negotiation of an approximately 180 degree turn through the aortic arch to allow the guiding catheter to descend into the aortic cusp where entry may be gained to either the left or the right coronary artery as desired.

After the guiding catheter is advanced to the ostium of the coronary artery to be treated by PTCA, a flexible guidewire is inserted into the guiding catheter through a balloon and advanced to the area to be treated. The guide wire provides the necessary steerability for lesion passage. The guidewire is advanced across the lesion, or "wires" the lesion, in preparation for the advancement of the balloon catheter across the guide wire. The balloon, or dilatation, catheter is placed in position by sliding it along the guide wire. The use of a relatively rigid guide wire is necessary to advance the catheter through the narrowed lumen of the artery and to direct the balloon, which is typically quite flexible, across the lesion. Radiopaque markers in the balloon segments of the catheter facilitate positioning across the lesion. The balloon catheter is then inflated with contrast material to permit fluoroscopic viewing during treatment. The balloon is alternately inflated and deflated until the lumen of the artery is satisfactory enlarged.

By way of example, further details of angioplasty procedures and devices used in such procedures can be found in U.S. Pat. No. 4,327,071 (Simpson et al.), U.S. Pat. No. 4,332,254 (Lundquist), U.S. Pat. No. 4,439,185 (Lundquist), U.S. Pat. No. 4,468,224 (Enzmann et al.), U.S. Pat. No. 4,516,972 (Samson), U.S. Pat. No. 4,582,181 (Samson), U.S. Pat. No. 4,748,982 (Horzewski et al.), U.S. Pat. No. 4,771,778 (Mar), and U.S. Pat. No. 4,793,350 (Mar et al.), each of which is hereby incorporated by reference herein.

A common problem that sometimes occurs after an angioplasty procedure is the appearance of restenosis at or near the site of the original stenosis in the blood vessel, which requires a secondary angioplasty procedure or bypass surgery. Another occurrence which reduces the success of angioplasty procedures is the collapse of a section of the dissected lining (commonly termed a "flap") into the blood stream upon deflation of the balloon, thereby closing or significantly reducing the blood flow through the vessel. In this instance, emergency bypass surgery is sometimes required to avoid a myocardial infarct distal blockage.

On some occasions, the dilatation catheter can be replaced with a perfusion type dilatation catheter such as described in U.S. Pat. No. 4,790,315 (Mueller, Jr. et al.) in order to hold the blood vessel open for extended periods. However, perfusion type dilatation catheters have relatively large profiles which can make advancement thereof through the blockage difficult, and therefore immediate bypass surgery may be the only means of avoiding an infarct distal to the blockage or possibly even death. Additionally, the inflated balloon of these perfusion catheters can block off a branch artery, thus creating ischemic conditions in the side branch distal to the blockage.

In recent years, various devices and methods for prevention of restenosis and repairing damaged blood vessels have been developed which typically use an expandable cage or region commonly termed a "stent" which is placed on the distal end of a catheter, and is designed to hold a detached lining against an arterial wall for extended periods to facilitate the reattachment thereof. Stents are generally cylindrically shaped intravascular devices which in some cases can also be used as the primary treatment devices where they are expanded to dilate a stenosis and then left in place.

Various types of stents and stent delivery systems are disclosed in U.S. Pat. No. 3,868,956 (Alfidi et al.), U.S. Pat. No. 4,503,569 (Dotter), U.S. Pat. No. 4,512,338 (Balko et al.), U.S. Pat. No. 4,553,545 (Maass et al.), U.S. Pat. No. 4,655,771 (Wallsten), U.S. Pat. No. 4,665,918 (Garza et al.), U.S. Pat. No. 4,733,665 (Palmaz), U.S. Pat. No. 4,795,458 (Regan), U.S. Pat. No. 4,800,882 (Gianturco), U.S. Pat. No. 4,830,003 (Wolff et al.), U.S. Pat. No. 4,856,516 (Hillstead), U.S. Pat. No. 4,878,906 (Lindemann et al.), U.S. Pat. No. 4,886,062 (Wiktor), U.S. Pat. No. 4,907,336 (Gianturco), U.S. Pat. No. 5,201,757 (Heyn et al.), U.S. Pat. No. 5,234,457 (Andersen), U.S. Pat. No. 5,292,331 (Boneau), U.S. Pat. No. 5,314,444 (Gianturco), U.S. Pat. No. 5,344,426 (Lau et al.), U.S. Pat. No. 5,372,600 (Beyar et al.), U.S. Pat. No. 5,387,235 (Chuter), U.S. Pat. No. 5,449,373 (Pinchasik et al.), U.S. Pat. No. 5,540,712 (Kleshinski et al.), U.S. Pat. No. 5,549,662 (Fordenbacher), U.S. Pat. No. 5,591,197 (Orth et al.), U.S. Pat. No. 5,593,434 (Williams), U.S. Pat. No. 5,599,576 (Opolski), U.S. Pat. No. 5,607,467 (Froix), U.S. Pat. No. 5,603,721 (Lau et al.), U.S. Pat. No. 5,605,530 (Fischell et al.), U.S. Pat. No. 5,382,261 (Palmaz), U.S. Pat. No. 5,549,635 (Solar), U.S. Pat. No. 5,500,013 (Buscemi et al.), U.S. Pat. No. 5,234,456 (Silvestrini), U.S. Pat. No. 5,342,348 (Kaplan), U.S. Pat. No. 5,368,566 (Crocker), U.S. Pat. No. 5,383,928 (Scott et al.), U.S. Pat. No. 5,423,885 (Williams), U.S. Pat. No. 5,443,458 (Eury), U.S. Pat. No. 5,464,450 (Buscemi et al.), U.S. Pat. No. 5,464,650 (Berg et al.), U.S. Pat. No. 5,618,299 (Khosravi et al.), U.S. Pat. No. 5,637,113 (Tartaglia et al.), U.S. Pat. No. 5,649,977 (Campbell), U.S. Pat. No. 5,419,760 (Narciso, Jr.), U.S. Pat. No. 5,651,174 (Schwartz et al.), and U.S. Pat. No. 5,556,413 (Lam), each of which is hereby incorporated by reference herein. See especially U.S. Pat. No. 4,800,882 to Gianturco, U.S. Pat. No. 5,234,457 to Andersen, U.S. Pat. No. 4,856,516 to Hillstead, and U.S. Pat. No. 5,500,013 to Buscemi et al.

Because it is of utmost importance to avoid thrombosis of the stent and its serious complications, patients who receive stents are often aggressively treated with anticoagulants such as heparin, aspirin, coumadin, dextran, and/or persantine. As expected, there is a high incidence of bleeding complications in these patients. A study performed at Emory University Hospital revealed that 33% of the patients who received stents for acute closure required transfusion, and 7% of the patients had an extremely large bleeding episode at the catheter entry site in the leg artery that necessitated surgical repair (Hearn et al., *J. Am. Coll. Cardiol.*, (1992).

Because of the complications associated with systemic treatment with anticoagulants, extensive attempts have been made to desing a stent that would be non-thrombogenic. A stent with little or no propensity to form thrombus would drastically decrease the need for aggressive treatment with anticoagulants. Initially, stents were constructed of plastic. Because all of these stents caused thrombosis, stainless steel was then tried. These stents appeared promising in studies in canine peripheral arteries. However, most coronary stents used to date in clinical trials are composed of stainless steel and yet still have a thrombotic occlusion rate of approximately 5–30%. Tantalum is another metal that is used in stents. Although initial reports of a lower thrombogenicity of tantalum stents appeared promising (van der Giessen et al., *Circulation*, 80:II-173 (1989)), more careful study has shown that tantalum is as thrombogenic as stainless steel (de Jaegere et al., *Amer. J. Cardiol.*, 69:598–602 (1992)).

The concept of coating a stent with a polymer was described several years ago and is discussed in the literature regularly. In the past, local delivery of drug(s) using stents has centered around two concepts: (1) directly coating the stent wires with a drug or a drug-polymer combination (Bailey et al., *Circulation*, 82:III-541 (1990); and Cavendar et al., *Circulation*, 82:III-541 (1990)); and (2) incorporating a drug into a stent that is constructed of a biodegradable polymer (Murphy et al., *J. Invasive Cardiol.*, 3:144–48 (1991)). Most investigators and stent companies have focussed their efforts on directly coating the metal stent wires with a polymer. This polymer is usually placed directly on the stent (e.g., by dipping the stent in soluble polymer) or is covalently bound to the metal. The polymer is bonded to or contains an anticoagulant compound most coated stents currently under development use heparin as their active agent. One of the more effective polymer coatings for stents is Biogold (van der Giessen, *Circulation*, 82:III-542 (1990)).

Significant difficulties have been encountered with all prior art stents. Each has its percentage of thrombosis, restenosis, and tissue in-growth problems, as well as various degrees of difficulty of deployment. Another difficulty is that many prior art stents do not conform well to the vessel lumen. Some prior art stents require administration of anticoagulant medication to the patient for up to three months following their placement inside the body. What has been needed and heretofore unavailable in the art is a stent that can be quickly and easily used in a wide variety of situations, that keeps the vessel open with a minimum degree of recoil and shortening lengthwise, that is flexible and can be delivered to the most distal lesion, and that can continuously deliver anticoagulant or other biologically active agents for an extended period directly at the site of stent placement.

SUMMARY OF THE INVENTION

The present invention fills the above-described needs in the art by providing a stent that can be quickly and easily used in a wide variety of situations, that keeps the vessel open with a minimum degree of recoil and shortening lengthwise, that is flexible and can be delivered to the most distal lesion, and that can continuously deliver biologically active agents for an extended period directly at the site of stent placement.

The present invention substantially reduces the complications and overcomes the limitations of prior art devices. In accordance with the present invention, there are provided flexible stents that can be delivered through a curved body conduit using a routine medical procedure and a conventional stent delivery system. Stents produced according to the present invention do not cause significant thrombosis at the point of implant, nor do they cause significant restenosis after implantation.

Thus, the present invention provides stents that have superior performance characteristics, as well as certain production advantages, as compared to prior art devices. Therefore, the articles and methods of the present invention are extremely useful in coronary artery balloon angioplasty, as well as related medical procedures where it is useful to provide a stent to any body lumen.

DETAILED DESCRIPTION OF THE INVENTION

The above features and advantages of the present invention, as well as others are accomplished by providing a stent comprising a flexible, serpentine backbone and a plurality of cavities capable of incorporating biologically active agents therein.

Also provided according to the present invention is a stent comprising at least one flexible, serpentine backbone and a plurality of opposing, outwardly-projecting appendages on said backbone; wherein said stent has a substantially circular cross-section.

Also provided according to the present invention is a method of producing a stent, said method comprising machining a sheet of material to create a leaving portion and a stent-forming portion, said stent-forming portion comprising at least one flexible, serpentine backbone and a plurality of opposing, outwardly-projecting appendages on said backbone, and shaping said stent-forming portion to have a substantially circular cross-section, thereby forming said stent.

Also provided according to the present invention is another method of producing a stent, said method comprising wrapping a length of wire around appropriately placed guideposts to create a pre-stent comprising at least one flexible, serpentine backbone and a plurality of opposing, outwardly-projecting appendages on said backbone, fastening the base of each of said appendages to said backbone, and shaping said pre-stent to have a substantially circular cross-section, thereby forming said stent.

Also provided according to the present invention is still another method of producing a stent, said method comprising machining a tube of material to create a leaving portion and a stent-forming portion, said stent-forming portion comprising at least one flexible, serpentine backbone and a plurality of opposing, outwardly-projecting appendages on said backbone.

While the primary application for stents according to the invention is presently treatment of cardiovascular disease such as atherosclerosis or other forms of coronary narrowing, stents according to the present invention may also be used for treatment of narrowing vessels in kidney lumens, respiratory lumens, urogenital lumens, bileducts, or elsewhere in the body. In such other vessels, the size of the stent may be adjusted to compensate for differing sizes of the vessel to be treated.

Figure 5:
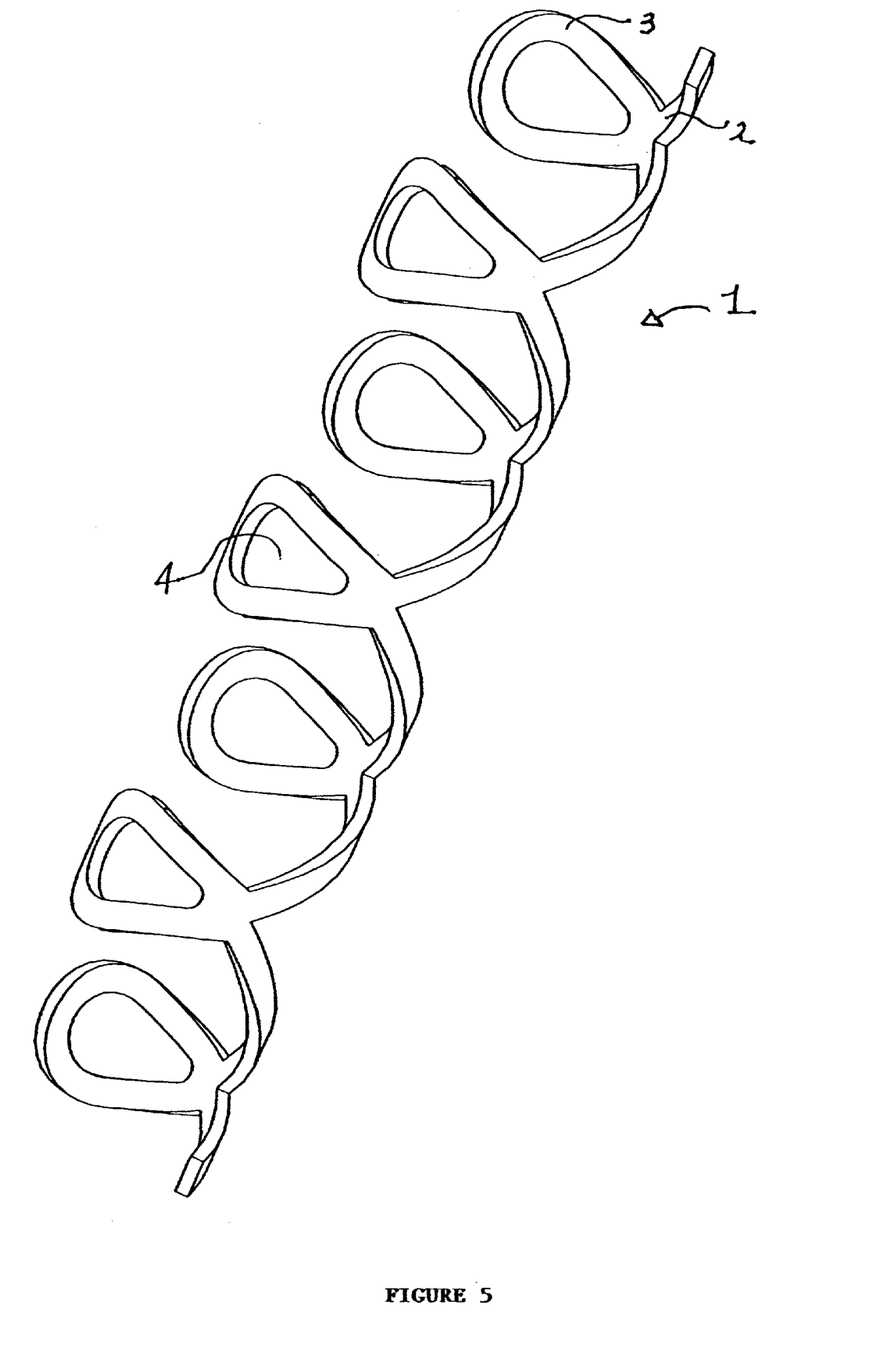
FIG. 5 is an elevation view of a stent according to the present invention, prior to placement and expansion within a body lumen.
Figure 6:
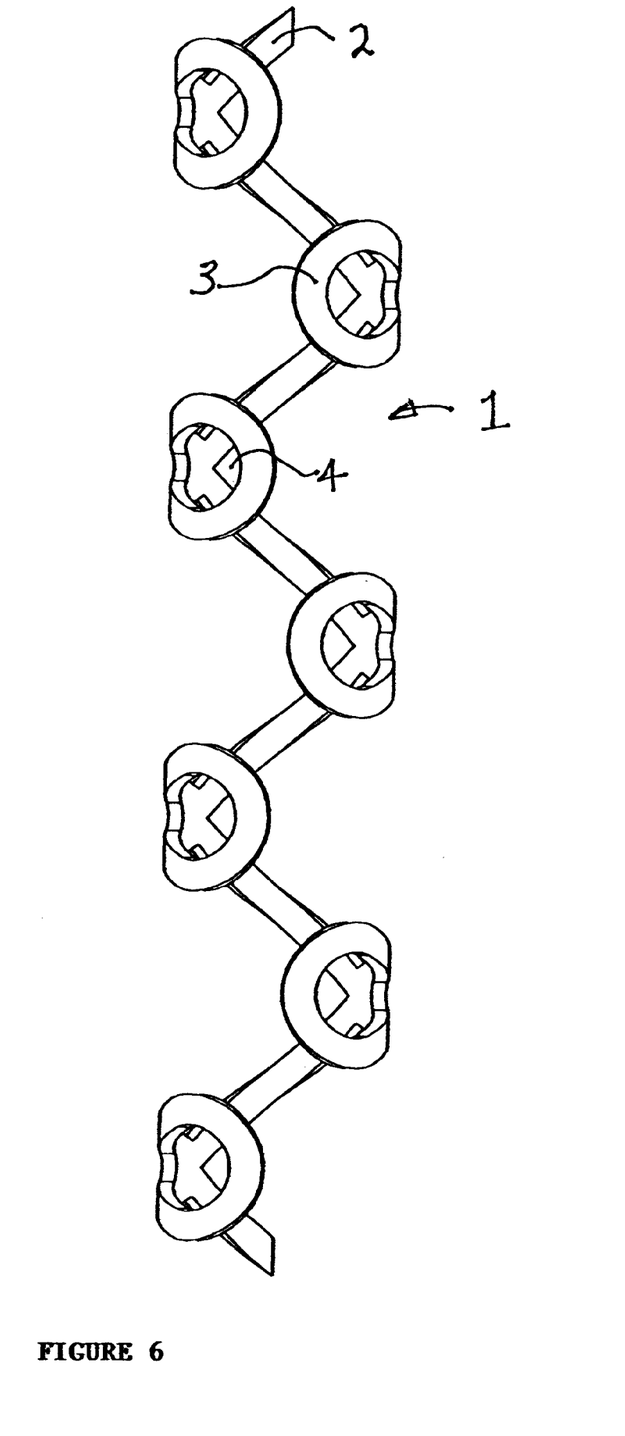
FIG. 6 is an elevation view of the stent of FIG. 5 as it would appear after placement and expansion.

Referring first to FIG. 5, one embodiment of a stent according to the invention is shown. A stent 1 comprises a semi-rigid, serpentine backbone 2 on which is attached several appendages 3. The dimensions and shape of the stent 1 can vary dramatically. Of course, a major factor in selecting stent size is the intended biological use thereof. Obviously, the dimensions of the body lumen into which the stent 1 will be placed is a primary factor in determining the preferred shape and size. However, generally speaking, it is preferred that the stent 1 have a circular cross-section throughout its length. Additionally, it is usually simplest and best if the stent 1 is generally, cylindrical in shape. In another preferred alternative embodiment, the stent 1 is frustoconical (i.e., lampshade-shaped), as this enables the stent 1 to be introduced into a body lumen narrow-end-first, thus allowing for easier transluminal movement of the stent 1. Of course, those of skill in the art can develop many alternative shapes that can be used as well.

It is generally preferred that the stent 1 has a length of about 6 mm to about 200 mm. In a more preferred embodiment, the stent 1 has a length of about 10 mm to about 25 mm. In a most preferred embodiment (especially with respect to vascular placement), the stent 1 has a length of about 12 mm to about 18 mm.

Although the stent 1 may be formed by first creating the backbone 2 and then attaching the appendages 3 thereto, it is presently preferred that the stent 1 be integrally formed from a single piece of material. By integrally formed, it is meant that the stent 1 is made from a single and continuous piece, sheet, tube, or other starting form of material, with no welds, adhesives, or other non-integral forms of attachment being used.

Stents according to the present invention may be formed of a variety of materials that have the appropriate characteristics of formability, strength, flexibility, melting point, and non-reactivity with biological components. Thus, preferred materials for construction of a stent according to the invention are MP-35N, nitinol, ELGILOY™, platinum, platinum-tungsten, platinum-nickel, platinum-rhenium, stainless steel, gold, tantalum, titanium aluminide, polyurethane, silicone elastomers, polytetrafluoroethylene, combinations thereof, and the like. Presently, MP-35N is the most preferred material for construction of a stent according to the invention.

Although the backbone 2 is shown in FIG. 5 as having a shape similar to a regular, repeating sine-wave, it may be of many different shapes and still be within the scope of the present invention. The advantage of the serpentine backbone 2, as contrasted with comparable elements in prior art devices, is its non-linear and therefore more flexible shape. By being non-linear, the backbone 2 has a plurality of built-in flex points. These flex points, and the resulting increase in flexibility, enhance the ability of the doctor to transluminally move a stent according to the invention through tortuous anatomy to the desired site of use. Thus, in addition to the regular sine-wave shape seen in FIG. 5, backbone 2 may also have successive curves or waves in a non-regular pattern (i.e., successive waves having variances in frequency and/or amplitude, in repeating or non-repeating patterns), successive corners of varying angles in repeating or non-repeating patterns, combinations of curves and corners, or the like.

Because the backbone 2 is non-linear, its length, as measured along the curve, is greater than the length of the stent 1 itself. In a preferred embodiment, the length of the backbone 2, as measured along the curve thereof, is about 1.5 to about 4 times longer than the stent 1. In a most preferred embodiment, the length of the backbone 2, as measured along the curve thereof, is about 2 to about 3 times longer than the stent 1.

While the backbone 2 is required to support the appendages 3, it is the appendages 3 that actually do the work of supporting the vessel into which the stent 1 is placed. The appendages 3 may be in a wide variety of shapes and sizes sufficient to support the vessel. It is generally preferred that the appendages 3 have a relatively large hole 4 therein, as can be clearly seen in FIG. 5. By having a large hole 4 in each appendage 3, the appendages 3 as a group can effectively support a larger surface area of the lumen, while not completely covering the tissue at that surface. Additionally, in preferred embodiments the appendages 3 are loop-shaped, rectangular, square-wave-shaped, teardrop-shaped, trapezoidal, rhomboidal, combinations thereof, or the like. In a presently preferred embodiment, the appendages 3 are loop-shaped.

As mentioned above, while a variety of sizes are possible, and the preferred size of the appendages 3 depends mostly upon the size of the lumen in which the stent 1 will be used, it is generally preferred that the appendages 3 have a length of about 5 mm to about 200 mm, and a width of about 0.5 mm to about 5 mm. In a presently preferred embodiment, the appendages 3 have a length of about 0.5 mm to about 5 mm and a width of about 0.5 mm to about 4 mm.

While not required, it is preferred that the appendages 3 be present down the entire length of the stent 1. It is generally preferred that each stent 1 includes about 5 to about 40 appendages thereon. In a presently preferred embodiment, each stent 1 includes about 10 to about 20 appendages thereon. Thus, it is generally preferred that the distance between each of the appendages 3 on a single stent 1 is about 0.1 mm to about 1.5 mm.

Because the appendages 3 do not interconnect to one another, they can be seen to permit the stent 1 to be compressed or expanded over a wide range of diameters while still maintaining the significant mechanical force required to prevent a vessel from recoiling or collapsing. While it is generally preferred that there be some degree of overlap between the appendages 3 extending from each side of the stent 1 (see FIG. 5) when the stent 1 is either expanded or contracted, this is not an absolute requirement.

The degree of radial compliance of a stent will be dependent upon the strength of the metal alloy, the thickness of the stent strud, the proximity of successive appendages (i.e., the inter-appendage interval), and the angle of orientation of the appendages.

Figure 4:
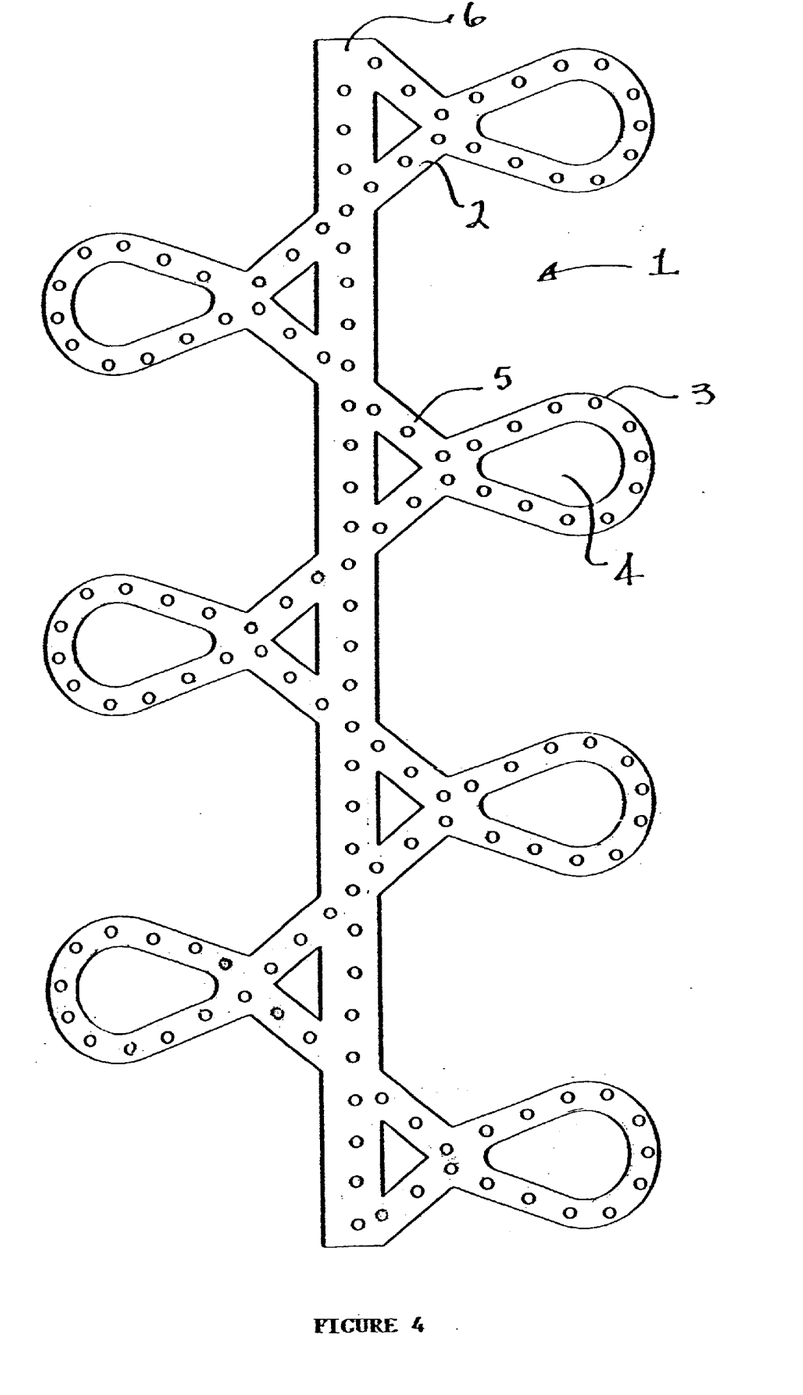
FIG. 4 is a plan view of an alternative embodiment of the partially-formed stent of FIG. 3, further including a secondary backbone in addition to the serpentine backbone.

In the presently preferred embodiment, the stent according to the present invention includes a plurality of cavities 5 thereon, as seen in FIG. 4. The cavities are essentially relatively small holes or craters in the stent that may be filled with a biologically active agent or biologically active agent-containing formulation. By pre-filling the cavities with a biologically active agent prior to placement of the stent, the biologically active agent will be released into the patient after placement. Because the biologically active agent will be released at the site of placement, the biologically active agent can have its greatest effects directly at the desired location, without prior dilution throughout the body of the patient.

Preferably, each stent 1 will include about 8 to about 400 cavities 5. While the cavities 5 may be of almost any three-dimensional size or shape, in a preferred embodiment the cavities 5 are essentially hemispherical, slit-like, cubical, rectangular, teardrop-shaped, or the like. In a presently preferred embodiment, the cavities 5 are essentially circular in shape. The size of the cavities 5 is relatively unimportant, as long as the cavities 5 are large enough to hold the desired amount of biologically active agent. However, it is presently preferred that each of the cavities 5 has a volume of about 0.02 mm$^3$ to about 4 mm$^3$.

The cavities 5 may contain any desired biologically active agent. The term "biologically active agent" is used herein in an extremely expansive sense, and generally indicates any biologically active or diagnostically useful substance, including drugs, radioactive chemicals, gene therapy vectors, and the like. Exemplary drugs for use in the present invention are heparin, tissue plasminogen activator, coumadin, protamine, urokinase, hirudin, argatroban, forskolin, vapiprost, prostacyclin, prostacyclin analogues, dextran, D-phe-pro-arg-chloromethylketone, dipyridamole, glycoprotein IIb/IIIa platelet membrane receptor antibody, angiopeptin, angiotensin converting enzyme inhibitors, (such as Captopril™, Cilazapril™, Lisinopril™), calcium channel blockers, colchicine, fibroblast growth factor antagonists, fish oil, omega 3-fatty acids, histamine antagonists, HMG-CoA reductase inhibitor, methotrexate, azathioprine, vincristine, vinblastine, fluorouracil, adriamycin, mutamycin, monoclonal antibodies, nitroprusside, phosphodiesterase inhibitors, prostaglandin inhibitor, seramin, serotonin blockers, steroids, thioprotease inhibitors, triazolopyrimidine and other PDGF antagonists, alpha-interferon, glucocorticoids, dexamethasone, betamethasone, tocopherol, aspirin, ticlopdine, ACA inhibitors, growth factors, oligonucleotides, antimitotic agents, antioxidants, antimetabolite agents, phosphorylcholine, antibiotics, anti-inflammatories, narcotics, anti-platelet drugs, cytostatic agents, antiproliferative agents, and the like. Exemplary radioactive chemicals include iridium, cesium, cobalt, and any other elements or compounds that contain radioactive isotopes. Presently, the most preferred biologically active agents are those that serve as anti-thrombus agents and/or anti-restenosis agents, as these are the most desirable biologically active agents for localization to the site of placement (when the stent 1 is used intravascularly).

The biologically active agent, or any formulation, containing the same, may be introduced into the cavities 5 by any suitable means known to those skilled in the art. For example, the stent 1 may be dipped into or otherwise coated with a liquid that includes the biologically active agent such that the liquid is drawn into the cavities 5 by surface tension affects. The liquid may subsequently be dried, or not, as desired. Alternatively, a biologically active agent in powder form may be "rubbed" into the cavities 5. As another alternative, the biologically active agent may be combined with a polymeric material having controlled-release properties, and each of the cavities 5 carefully filled with this mixture. Many other alternatives will occur to those of skill in the art. Furthermore, the biologically active agent may be added to the cavities 5 either as part of the manufacturing process, or immediately prior to placement of the stent 1 in a body lumen.

In one embodiment, the cavities 5 do not extend through the entire thickness of the stent 1. In this case, the cavities 5 might be best described as craters, as opposed to holes. In such embodiments, the cavities 5 may be present on only an inner surface of the stent 1, on only an outer surface of the stent 1, or both surfaces simultaneously. When the stent 1 has cavities 5 on both its inner surface and outer surface, the stent 1 may contain a first biologically active agent in those cavities 5 on the inner surface, and a second biologically active agent in those cavities 5 on the outer surface. In such an embodiment, it is preferred that the first biologically active agent is an anti-thrombus agent, and the second biologically active agent is an anti-restenosis drug.

Instead of, or in addition to, the use of cavities 5, the stent according to the present invention may include a biologically active agent-impregnated polymeric material coating all or a portion of the appendages 3. As is known to those of skill in the art, a wide variety of polymeric materials can either be formed with a releasable biologically active agent therein, or a biologically active agent may be absorbed by the polymeric material after its formation. By coating the appendages 3 with such a biologically active agent-impregnated polymeric material prior to placement inside a biological lumen, the biologically active agent may be released at the site of placement. As an example, see U.S. Pat. No. 5,605,696 (Eury et al.).

According to the present invention, novel methods for producing a stent have also been developed. A first such method, as shown in FIGS. 1–3 and 5, comprises machining a sheet of material 10 to create a leaving portion 11 and a stent-forming portion 12, said stent-forming portion 12 comprising at least one flexible, serpentine backbone 2 and a plurality of opposing, outwardly-projecting appendages 3 on said backbone 2, and then shaping said stent-forming portion 12 to have a substantially circular cross-section, thereby forming said stent 1.

Figure 1:
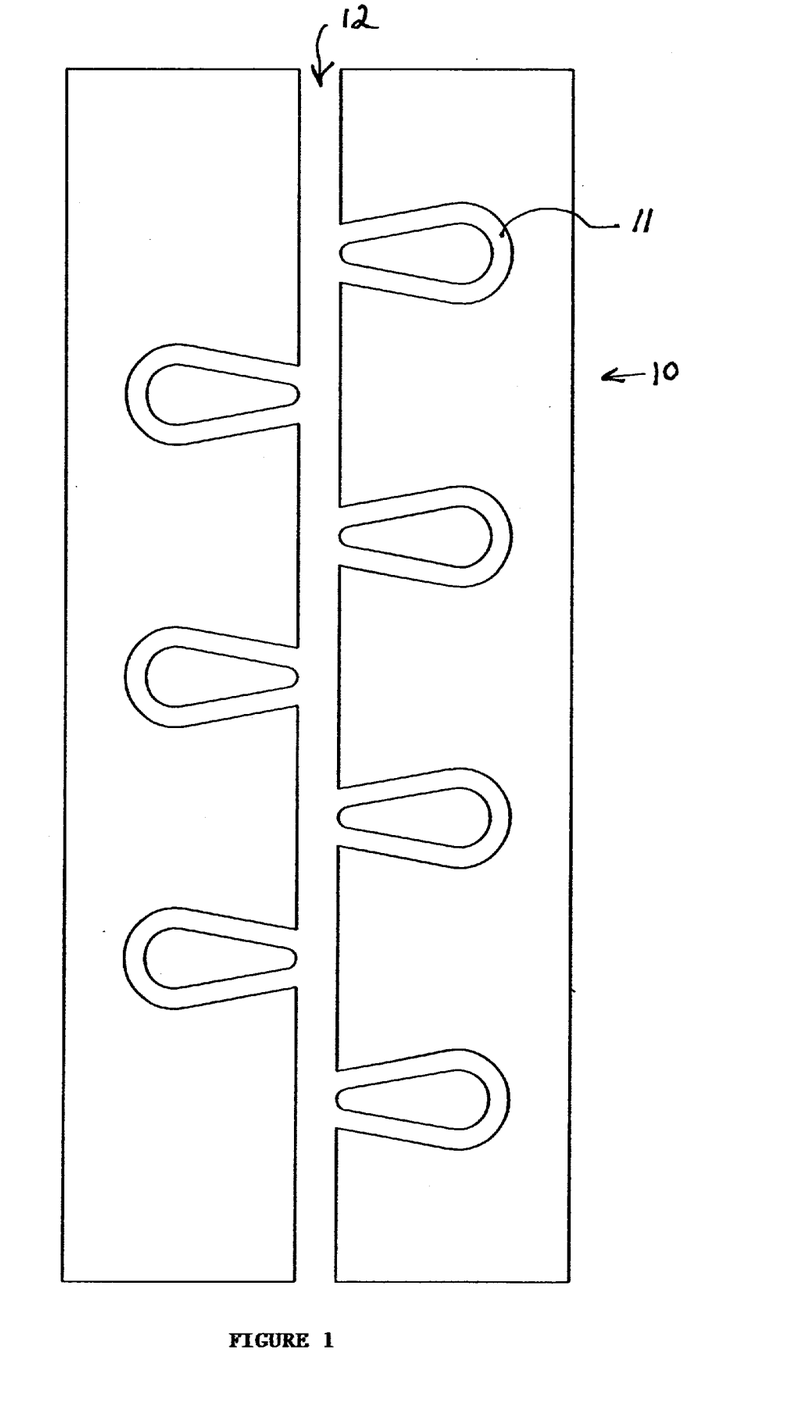
FIG. 1 is a plan view of a sheet of material to be used to form a stent according to the present invention, wherein the pattern of material to be removed is shown.

Thus, according to this first method, one starts with a preferably planar sheet of material 10, as best seen in FIG. 1 (which shows the pattern where the leaving portion 11 and the stent-forming portion 12 will be machined). The sheet of material 10 can be machined in any of a variety of ways, including laser-cutting, photo-chemical etching (discussed in more detail below), mechanical cutting, other mechanical methods, and the like. The machining process separates the sheet of material 10 into the leaving portion 11, which is typically recycled, and the stent-forming portion 12, which is further processed to create the stent 1.

Figure 2:
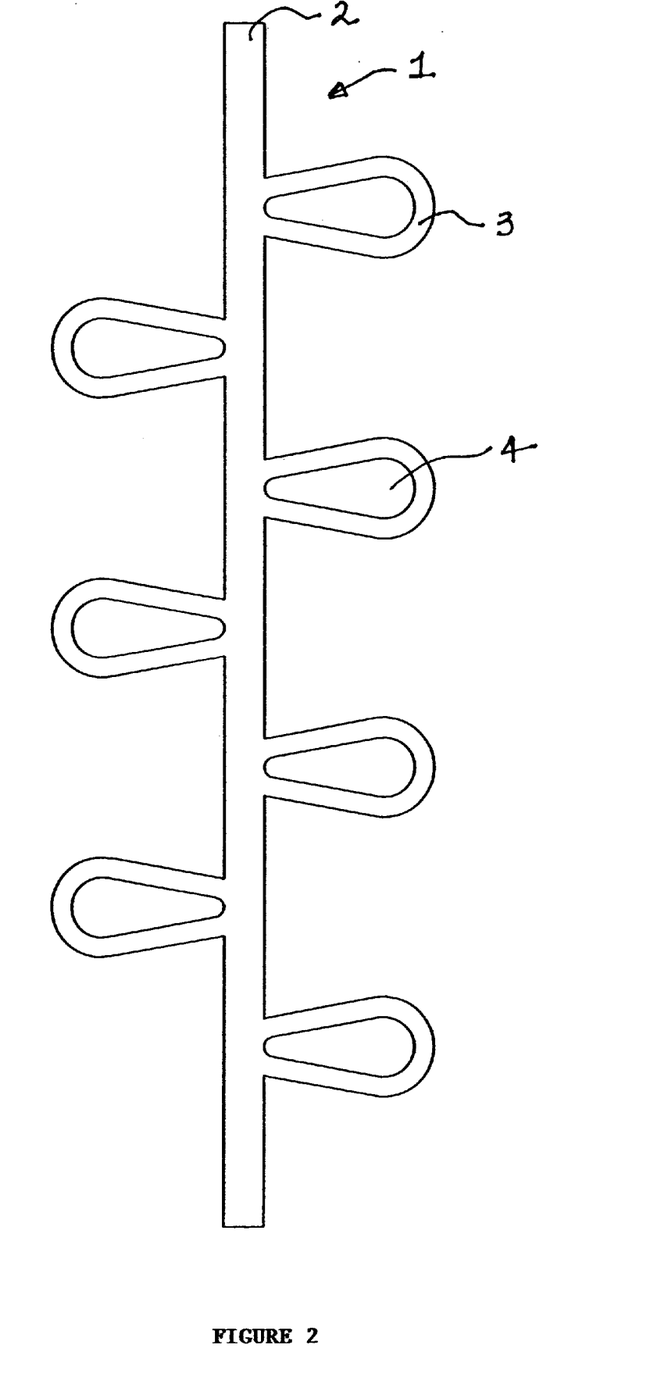
FIG. 2 is a plan view of a partially-formed stent according to one embodiment the present invention, wherein the appropriate portions of the sheet of material have been removed.

The partially-formed stent 1, as seen in FIG. 2, is next processed by bending the backbone 2 thereof in order to introduce the necessary curves or corners. This may be done by any means now known or later developed by those of skill in the art. It is also possible to avoid this bending step entirely by machining the sheet of material 10 such that the backbone 2 of the stent-forming portion 12 is already serpentine at the conclusion of the machining step.

An alternative embodiment of the present invention is seen in FIG. 4. In this embodiment, the stent 1 has two backbones, the serpentine backbone 2 as previously described, and a linear backbone 6. The advantages of adding the linear backbone 6 include increased structural integrity, minimization of length changes upon deployment, and the like. In a modification of this embodiment, the linear backbone 6 is discontinuous. By discontinuous it is meant that the linear backbone 6 is comprised of a series of physically separate linear pieces connecting consecutive portions of the serpentine backbone 2, but not every consecutive portion. This modification results in a stent having properties that are typically intermediate between the embodiment shown in FIG. 4, and that of FIG. 3.

The linear backbone 6 may be added to the stent 1 in many ways. The simplest and preferred method is to perform the machining step such that the serpentine backbone 2 and the linear backbone 6 are produced simultaneously. The main advantage of this method is the fact that the integral nature of the stent 1 is maintained. A second method is to weld or otherwise adhere the linear backbone 6 to the partially formed stent as seen in FIG. 3.

Figure 3:
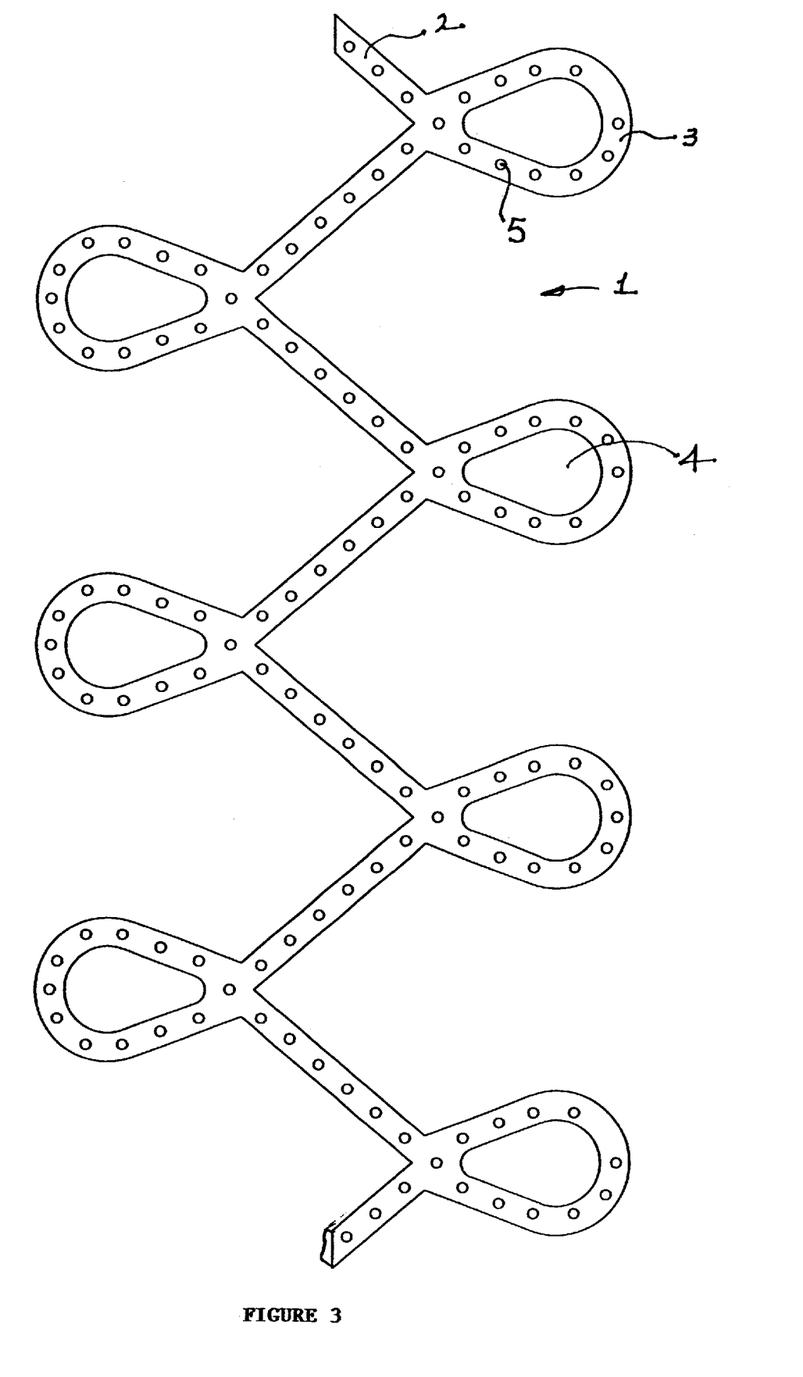
FIG. 3 is a plan view of a partially-formed stent according to one embodiment the present invention, wherein the partially-formed stent of FIG. 2 has been bent to create the serpentine backbone, and the cavities have been added.

The final step in forming the stent 1 is the curling of the partially formed stent 1 (as seen in FIG. 3 or 4) into a cylindrical or frustoconical shape, thus forming the finished stent 1. There are many methods of performing this step that are well known to those of skill in the art, any of which will suffice.

Another step that is preferably performed is the machining of the sheet of material 10 to include cavities 5 in the stent-forming portion 12. This step may be performed in a wide variety of ways, e.g., by laser, chemical, or mechanical means known to those of skill in the art, and the like. Although this step may be performed at any time, it is presently preferred to machine the cavities 5 in the sheet of material 10 prior to any other production step. However, the formation of the cavities 5 may be done at any stage of production, if desired.

A preferred method of machining the sheet of material 10 to create the leaving portion 11 and the stent-forming portion 12 is photochemical etching, comparable to the techniques used in the microchip industry. The first step in this method is to coat the sheet of material 10 with a layer of photoresist or similar such coating compound. Next, a template with the design of the stent 1 is placed over the sheet of material 10. Then, the photoresist is removed from those areas not covered by the template. This is preferably done by laser, although other techniques are well known to those of skill in the art. Finally, the sheet of material 10 is chemically etched or chemically milled, thereby removing the leaving portion 11 and creating the stent-forming portion 12.

In an alternative method for producing a stent 1 according to the present invention, a tube of material can be machined to create a leaving portion and a stent-forming portion, which are similar in nature to the leaving portion 11 and the stent-forming portion 12 as discussed above. The major difference in this method is that the final forming step is not required, as the tubular nature of the starting material means that the stent 1 is in finished form as soon as the leaving portion is removed. Just as above, using this method, the stent-forming portion comprises at least one flexible, serpentine backbone 2 and a plurality of opposing, outwardly-projecting appendages 3 on the backbone 2.

In another alternative method for producing a stent 1 according to the present invention, a length of wire can be wrapped around appropriately placed guideposts to create a pre-stent comprising at least one flexible, serpentine backbone 2 and a plurality of opposing, outwardly-projecting appendages 3 on the backbone 2. Then, the pre-stent is shaped to have a substantially circular cross-section, thereby forming the stent 1.

As discussed above, memory metals such as nitinol may be used to produce a stent according to the invention. As such, it is useful to set the memory of the metal to a specific shape at some point during manufacture. This is preferably done by heat-treating the metal. Once the metal is in the desired shape, it is subjected to heat of about 980±20° F., for about one to five hours. This is typically sufficient to adjust the crystal lattice of the metal and thereby set the memory. Of course, other temperatures, for different periods of time, may be desirable for memory metals other than nitinol.

In accordance with another embodiment of the present invention, there are provided methods for delivering a biologically active agent to a patient, comprising inserting the stent 1 according to the present invention (specifically, those embodiments that include cavities 5) into a vessel of the patient.

While the invention has been described in detail with reference to certain preferred embodiments thereof, it will be understood that modifications and variations are within the spirit and scope of that which is described and claimed.

What is claimed is:

1. A stent comprising:
   a) a flexible, serpentine backbone defining a longitudinal axis of a substantially tubular member; and
   b) a plurality of cavities integral to an inner and an outer surface of said backbone, wherein said cavities on said inner surface of said stent contain a first biologically active agent, and said cavities on said outer surface of said stent contain a second biologically active agent, wherein said first biologically active agent is different from said second biologically active agent.

2. A stent according to claim 1, wherein said first biologically active agent is an anti-thrombus agent, and said second biologically active agent is an anti-restenosis drug.

* * * * *